(12) United States Patent
Pak et al.

(10) Patent No.: US 10,864,023 B2
(45) Date of Patent: Dec. 15, 2020

(54) SURGICAL IMPLANT PREPARATION SYSTEM AND METHOD

(71) Applicant: CLARIANCE SAS, Beaurains (FR)

(72) Inventors: Shane S. Pak, Arcadia, CA (US); Karlton E. Spindle, Cedar Glen, CA (US)

(73) Assignee: CLARIANCE SAS, Beaurains (FR)

( * ) Notice: Subject to any disclaimer, the term of this patent is extended or adjusted under 35 U.S.C. 154(b) by 0 days.

(21) Appl. No.: 16/140,491

(22) Filed: Sep. 24, 2018

(65) Prior Publication Data

US 2019/0336179 A1    Nov. 7, 2019

Related U.S. Application Data

(60) Provisional application No. 62/762,478, filed on May 7, 2018.

(51) Int. Cl.

| | | |
|---|---|---|
| *A61B 17/70* | (2006.01) | |
| *A61B 17/88* | (2006.01) | |
| *A61B 34/10* | (2016.01) | |
| *G06F 17/50* | (2006.01) | |
| *G16H 20/40* | (2018.01) | |
| *G06F 30/20* | (2020.01) | |
| *A61B 17/00* | (2006.01) | |

(52) U.S. Cl.
CPC ...... *A61B 17/7074* (2013.01); *A61B 17/7031* (2013.01); *A61B 17/7032* (2013.01); *A61B 17/8863* (2013.01); *A61B 34/10* (2016.02); *G06F 30/20* (2020.01); *G16H 20/40* (2018.01); *A61B 2017/00057* (2013.01); *A61B 2034/104* (2016.02); *A61B 2034/108* (2016.02)

(58) Field of Classification Search
CPC ............ A61B 17/7074; A61B 17/7031; A61B 7/7032; A61B 7/8863; A61B 7/1757; A61B 7/1703; A61B 34/10; A61B 34/20; A61B 34/25; A61B 90/37; A61B 2017/00057; A61B 2034/104; A61B 2034/108; A61B 2034/2055; A61B 2090/3983; A61B 2090/374; A61B 2090/3762; A61B 2090/364; A61B 2090/363; A61B 2090/3916; A61B 2090/367; A61B 2090/376; G16H 20/40; G06F 17/5009
USPC .................................. 606/246–279, 300–328
See application file for complete search history.

(56) References Cited

U.S. PATENT DOCUMENTS

| | | |
|---|---|---|
| 3,661,002 A | 5/1972 | Peddinghaus, Jr. |
| 3,821,525 A | 6/1974 | Eaton et al. |
| 4,785,650 A | 11/1988 | Lusty |
| 4,825,678 A | 5/1989 | Post |
| 5,447,432 A | 9/1995 | Andreiko et al. |
| 6,035,691 A | 3/2000 | Lin et al. |

(Continued)

FOREIGN PATENT DOCUMENTS

KR    101137991 B1    4/2012

OTHER PUBLICATIONS

International Search Report issued in International Application No. PCT/US2019/030489 dated Sep. 11, 2019.

(Continued)

*Primary Examiner* — Pedro Philogene

(74) *Attorney, Agent, or Firm* — Nixon & Vanderhye

(57) ABSTRACT

A system to precisely contour a surgical implant based on intraoperative information is disclosed.

16 Claims, 8 Drawing Sheets

(56) References Cited

U.S. PATENT DOCUMENTS

| | | | |
|---|---|---|---|
| 6,434,995 B1 | 8/2002 | Kataoka et al. | |
| 9,039,772 B2 | 5/2015 | Park et al. | |
| 9,867,721 B2 * | 1/2018 | Hunter | A61B 17/025 |
| 9,872,715 B2 | 1/2018 | Crawford et al. | |
| 10,194,993 B2 * | 2/2019 | Roger | A61B 34/20 |
| 2004/0072120 A1 | 4/2004 | Lauren | |
| 2005/0262911 A1 * | 12/2005 | Dankowicz | B21D 7/14 |
| | | | 72/31.04 |
| 2007/0227216 A1 | 10/2007 | Schalliol | |
| 2009/0249851 A1 | 10/2009 | Isaacs | |
| 2013/0268007 A1 | 10/2013 | Rezach et al. | |
| 2013/0345757 A1 * | 12/2013 | Stad | A61B 17/7011 |
| | | | 606/279 |
| 2016/0210374 A1 | 7/2016 | Mosnier et al. | |
| 2017/0196508 A1 | 7/2017 | Hunter | |
| 2018/0289396 A1 * | 10/2018 | McGahan | A61B 34/20 |
| 2019/0209080 A1 * | 7/2019 | Gullotti | A61B 90/39 |

OTHER PUBLICATIONS

Abul-Kasim, K. and Ohlin, A., "The rate of screw misplacement in segmental pedicle screw fixation in adolescent diopathic scolios," Acta Orthopaedica, Feb. 2011; 82(1): 50-55.

Irrimax Corporation, "System Toxicity in Mice," Clinical In-Vivo Studies, IrriSept Wound Debridement and Cleansing System, IRR206 Acute Systemic/Neuro Tox Jun. 4, 2014, URL:http://1h3b4ucn10q31u8zvap66416.wpengine.netdna-cdn.com/wp-content/uploads/2.4_IRR206-Acute-Systemic-Neuro-Tox-2014-06-04.pdf.

Irrimax Corporation, "Irrisept Wound Debridement and Cleansing System Initial Safety Studies," IRR2009InitialSafetyStudies03262015, URL:http://1h3b4ucn10q31u8zvap66416.wpengine.netdna-cdn.com/wp-content/uploads/initial-safetystudies.pdf.

Tohmeh, A. et al., "Long Construct Pedicle Screw Reduction and Residual Forces are Decreased Using a Computer-Assisted Spinal Rod Bending System," The Spine Journal 14 (2014) 143S-144S.

* cited by examiner

SURGICAL IMPLANT PREPARATION SYSTEM AND METHOD

CROSS-REFERENCE TO RELATED APPLICATION

This application claims the benefit of U.S. Provisional Application No. 62/762,478 filed May 7, 2018, the contents of which are incorporated herein by reference.

COPYRIGHT STATEMENT

This patent document contains material subject to copyright protection. The copyright owner has no objection to the reproduction of this patent document or any related materials in the files of the United States Patent and Trademark Office, but otherwise reserves all copyrights whatsoever.

FIELD OF THE INVENTION

This invention relates to the preparation of surgical implants, including the three-dimensional forming of surgical implants.

BACKGROUND OF THE INVENTION

Thousands of spinal stabilization surgeries are performed every year. During the procedures, stabilizing structures, such as spinal rods and/or plates, are implanted to provide support to and/or to correct undesirable curvatures of the patient's spine. The procedures may also involve the use of pedicle screws that may be embedded into the patient's spine to secure the rods/plates.

The pedicle screws may first be implanted, and the spinal rods may then be attached to the screws. Because the screws may not be perfectly aligned linearly, the spinal rod may require contouring (e.g., bending) to properly fit between the screws and to fit the desired curve of the spine.

One common method for contouring spinal rods is to bend them manually. The desired curvature of the rod may be determined by first placing a temporary flexible surrogate rod into the heads of the pedicle screws and bending the surrogate rod by hand to fit between the screws. The surrogate rod may then be removed and used as a visual guide to bend a primary surgical rod while using a manual rod-bending tool.

This procedure is subjective and may lead to metal fatigue of the primary spinal rod if the rod is accidentally over-bent and then re-bent in the opposite direction. In addition, the handheld rod bending tools may cause surface damage to the spinal rods during the bending process, resulting in local stress riser points and potential rod breakage after implantation. This method is also time-consuming, especially for inexperienced surgeons, and may undesirably extend the amount of time the patient may be required to be under anesthesia.

Another method of contouring spinal rods may be to use fluoroscopic images taken of the patient's spine prior to the surgery to create models (representations) of the patient's spine. The models may then be used to theoretically predict where the pedicle screws may be implanted, and the contour that the spinal rod may require to properly fit between them.

The spinal rod may then be contoured by hand or by a machine prior to the surgical procedure. However, it is very common that, due to anatomical variations of the patient's spine, the pedicle screws may not be implanted in the exact positions and orientations as modeled. In addition, the patient's spine may also shift and/or change position from the time of the pre-surgical imaging to the time of the surgical procedure. Given this, a pre-contoured spinal rod based on the pre-surgical images may not properly fit between the implanted pedicle screws and/or may not follow the desired curvature of the patient's spine.

When this happens, the pre-contoured spinal rods may require reworking, which may cause damage to the rods and extend the time the patient may be required to be under anesthesia. In addition, ill-fitting spinal rods may cause undesirable stress and strain to the patient's spine that may lead to significant health problems. Misfitting spinal rods may also apply undesirable strain on the pedicle screws and/or the spinal rod itself, causing the screws to dislodge from the spine and/or the rod to fail.

Accordingly, there is a need for a system and method that contours a spinal rod based on the intraoperative positions of the implanted pedicle screws and that of the patient's spine. There is also a need for a system and method to create precisely contoured spinal rods without damaging the rods. There is also a need to quicken the contouring of the rods to minimize the amount of time the patient may be required to be under anesthesia, and to reduce the overall costs of the surgical procedures.

SUMMARY OF THE INVENTION

The present invention is specified in the claims as well as in the below description.

In one embodiment, a system for intraoperatively contouring a spinal rod for placement onto the spine of a patient may include a contoured surrogate spinal rod, a scanning assembly configured to scan the contoured surrogate spinal rod and to output a first model based on the scan, a controller configured to receive the first model and to perform at least one analysis on the first model, and a contouring assembly configured to receive the first model from the controller and to contour the spinal rod based on the first model.

In one aspect, the controller may be configured to provide feedback relating to the results of the at least one analysis of the first model.

In another aspect, the contour of the contoured surrogate spinal rod may be based at least in part on the intraoperative position of one or more pedicle screws implanted into the patient's spine.

In another aspect, the at least one analysis of the first model may be based at least in part on the intraoperative position of the one or more pedicle screws and the position of the patient's spine.

In another aspect, the at least one analysis of the first model may be chosen from the group: load bearing analysis, stress analysis and failure analysis.

In another aspect, the controller may create a second model based at least in part on the first model, the intraoperative position of the one or more pedicle screws and the position of the patient's spine.

In another aspect, the controller may perform at least one analysis of the second model.

In another aspect, the at least one analysis on the second model may be chosen from the group: load bearing analysis, stress analysis and failure analysis.

In another aspect, the controller may compare the results of the at least one analysis on the second model with the pull-out strength of the one or more pedicle screws.

In another aspect, the controller may be configured to provide feedback relating to the results of the at least one analysis of the second model.

In another aspect, the controller may be configured to provide feedback relating to the comparison between the pull-out strength of the one or more pedicle screws and the results of the at least one analysis of the second model.

In another aspect, the scanning assembly may be a three-dimensional scanner.

In another aspect, the contouring assembly may be a rod bending machine.

In another aspect, the first model may be a three dimensional model of the contoured surrogate spinal rod.

In one embodiment, a method for intraoperatively contouring a spinal rod using a system that may include a contoured surrogate spinal rod, a scanning assembly, a controller, and a contouring assembly, may include:

(A) using the scanning assembly, scanning the contoured surrogate spinal rod to create a first model;

(B) using the controller, performing at least one analysis on the first model created in (A);

(C) using the controller, providing feedback relating to the results of the at least one analysis performed in (B);

(D) providing the first model to the contouring assembly; and (E) using the contouring assembly, contouring the spinal rod based on the model created in (A).

In one aspect, the at least one analysis in (B) may be chosen from the group: load bearing analysis, stress analysis and failure analysis.

In another aspect, the method may also include:

(B)(1) using the controller, creating a second model based at least in part on the first model, the intraoperative position of one or more pedicle screws implanted into the patient's spine, and the position of the patient's spine.

In another aspect, the method may also include:

(B)(2) using the controller, performing at least one analysis on the second model.

In another aspect, the at least one analysis in (B)(2) may be chosen from the group: load bearing analysis, stress analysis and failure analysis.

A person of ordinary skill in the art will understand, that any method described above or below and/or claimed and described as a sequence of steps is not restrictive in the sense of the order of steps.

BRIEF DESCRIPTION OF THE DRAWINGS

Various objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

In general, the system and method according to exemplary embodiments hereof provides systems and methods to assist in the preparation of surgical implants during surgical procedures. The preparation may include, but is not limited to, forming, contouring, bending or otherwise physically manipulating the surgical implant(s). The surgical procedures may include, but are not limited to, spinal stabilization surgery, facial and/or skull reconstruction, long bone reconstruction, pelvic fracture reconstruction, custom shaped joint reconstruction, as well as other types of surgical procedures. The surgical implants may include, but are not limited to, rods, plates, cages, joints, custom implants and other types of implants.

As is known in the art, prior to the placement of an implant, it may be preferable that the implant be properly prepared. For example, it be necessary to properly contour (e.g., bend, manipulate or otherwise form) the implant so that it may properly fit in its desired position within the patient's body. It is understood by a person of ordinary skill in the art that it may be preferable to prepare the implants with a high level of precision so that the shape, contour and form of the implants precisely match the position within the patient's body that may receive them. It is also understood that an implant with low precision may cause significant health problems to the patient and may need to be replaced and/or revised, requiring additional surgeries and causing additional complications.

For the purposes of this specification and for demonstration, the system and method will be described in relation to its use with surgical implants, for example, those used during spinal stabilization surgery (e.g., spinal rods). However, it will be understood by a person of ordinary skill in the art, upon reading this specification, that the system and method may be used with any type of surgical procedure and any type of surgical implant, and that the scope of the system and method is not limited in any way by the types of surgical procedures and/or the types of surgical implants that it may be used with.

In one exemplary embodiment hereof, the surgical implant may include a spinal rod used in spinal surgery to stabilize a particular vertebral segment of the patient's spine. Spinal rods may also be used to correct undesirable curvatures of the spine. Pedicle screws may first be implanted into adjacent vertebral bodies of the patient's spine, and the spinal rod may then be attached to the heads of the screws. In this way, the rod may be generally aligned and attached parallel to the spinal column thereby providing support to the spine.

Figure 1:
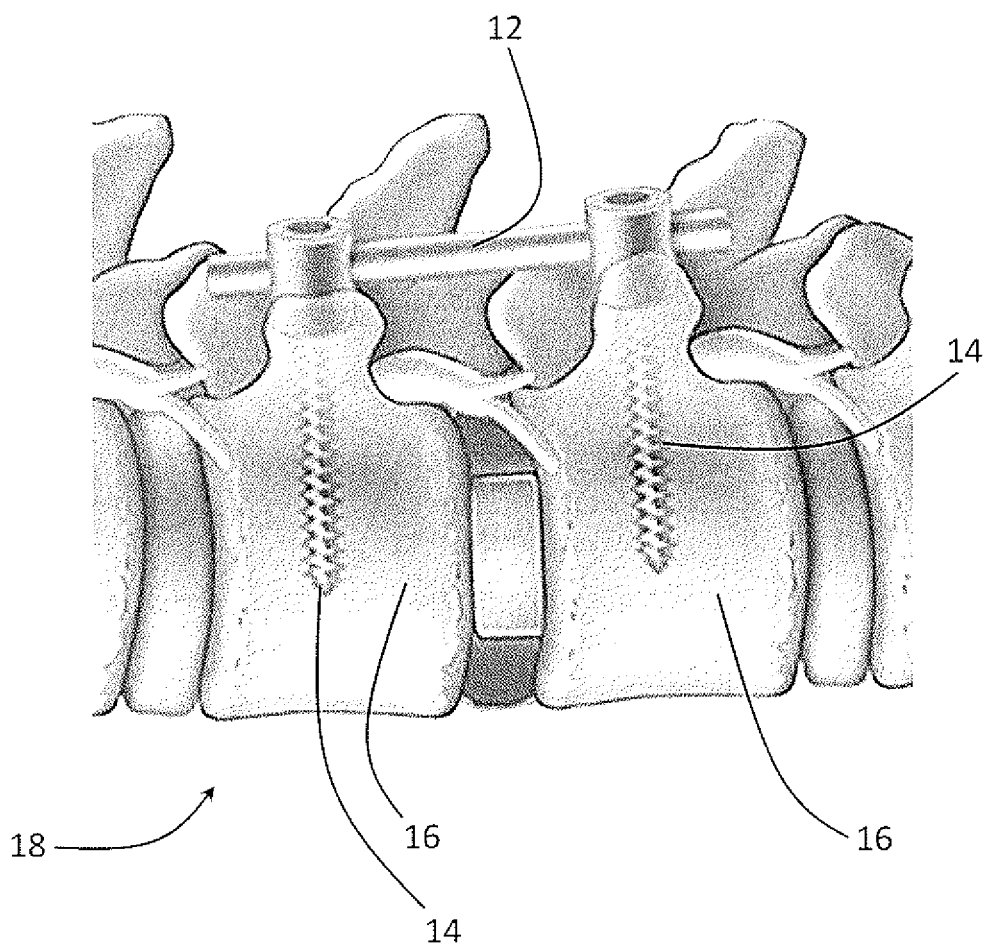
FIGS. 1 and 2 show aspects of pedicle screws and a rod according to exemplary embodiments hereof.

FIG. 1 shows a spinal rod 12 attached to two pedicle screws 14 that are embedded into adjacent vertebral bodies 16 of the patient's spine 18. While two pedicle screws 14 are shown supporting the spinal rod 12, other numbers of pedicle screws 14 may be used with any number of spinal rods 12.

Because of anatomical variations within the patient's spine 18 however, the implanted pedicle screws 14 may not be precisely linearly aligned with one another. As a result, prior to attachment to the screws 14, the spinal rod 12 may require contouring (e.g., bending or otherwise forming) in order to properly fit between them. Once contoured and attached, the spinal rod 12 may follow the path between the screws 14 and preferably not exert undesirable strain, torque or pressure to the screws 14 and/or to the patient's spine 18. The contour of the spinal rod 12 may also be used to correct for undesirable curvatures of the patient's spine.

Figure 2:
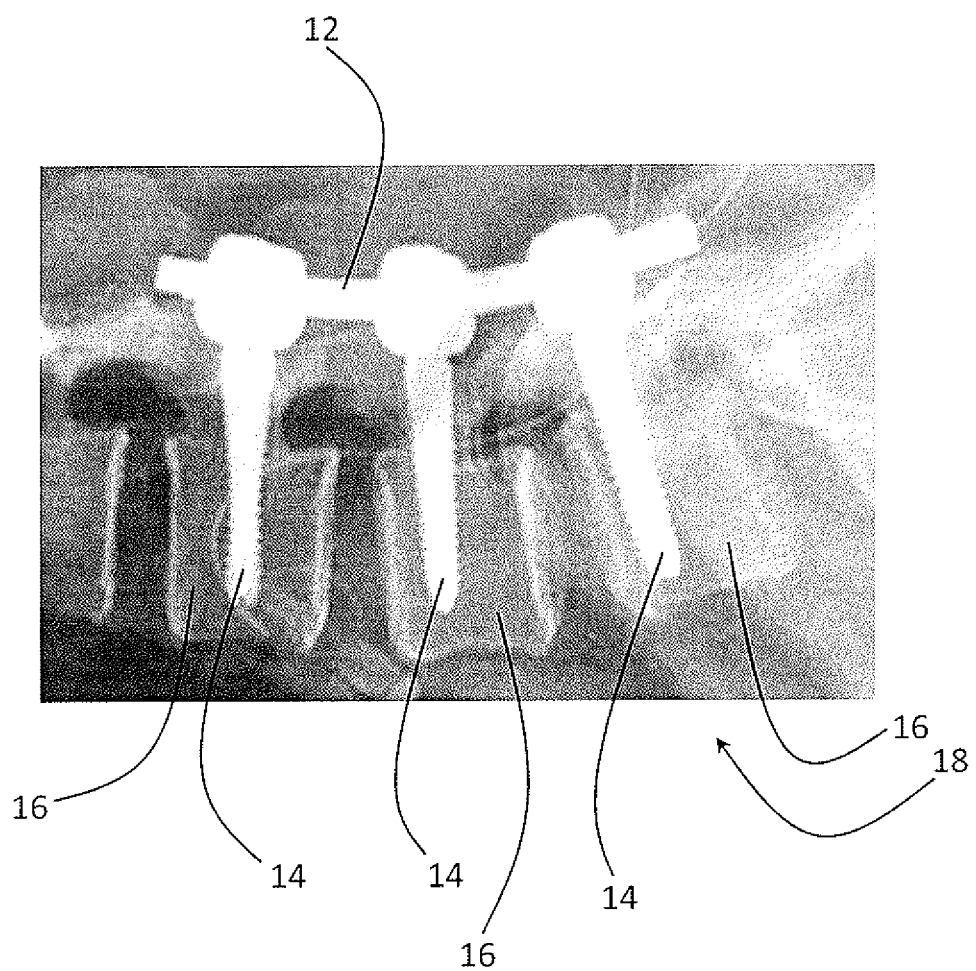

FIG. 2 shows an x-ray taken of three pedicle screws 14 implanted into a patient's vertebral bodies 16, and a spinal rod 12 attached between them. Note that the spinal rod 12 has a contour that generally matches the path between the screws 14 and that of the patient's spine 18.

Referring now to FIGS. 1-8, the system 10 according to exemplary embodiments hereof will be described in further detail. In general, the system 10 may provide a precisely formed surgical implant, such as a precisely formed spinal rod 12, that may be used in such surgical procedures.

Figure 3:
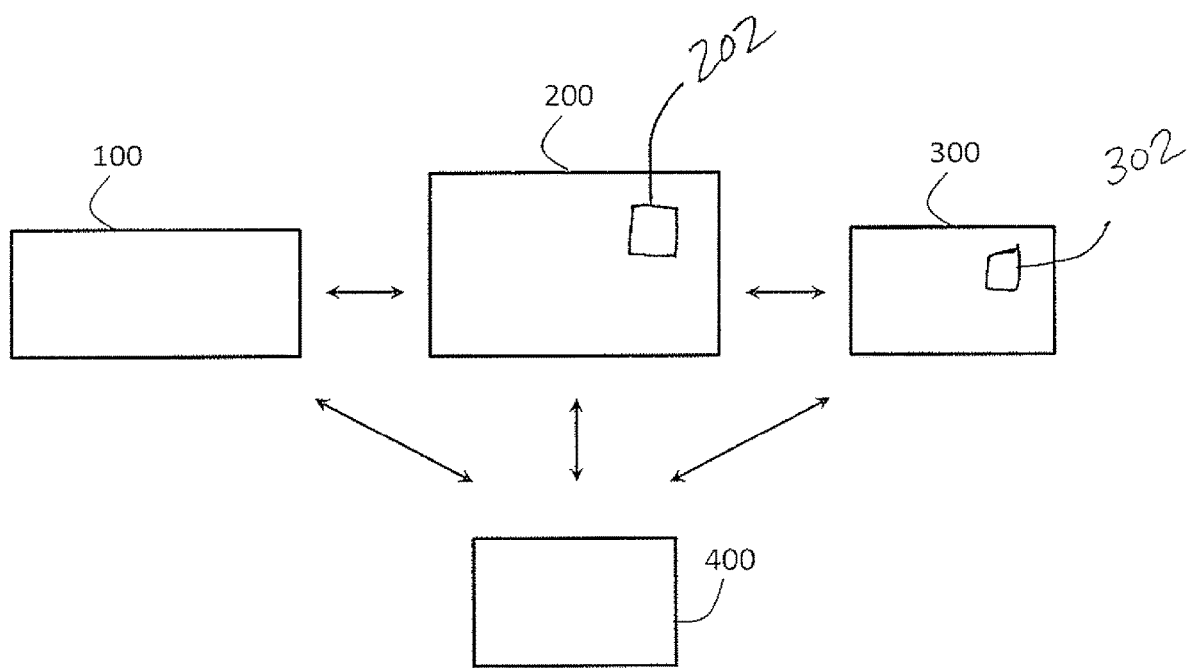
FIGS. 3-5 show aspects of a spinal rod contouring system according to exemplary embodiments hereof.

In one exemplary embodiment hereof as shown in FIG. 3, the system 10 may include a scanning assembly 100, a contouring assembly 200, a sterilization assembly 300, a controller 400 and other elements, components and mechanisms as necessary to perform its various functionalities.

The controller 400 may include any type of controller 400 including but not limited to: a tablet computer, a smartphone, a mobile device, a laptop computer, a PC, a networked controller, a server (e.g., a network, backend or cloud platform), a micro-controller and any other types or combinations of types of controller 400. The controller 400 may also include software, drivers, scripts and other types of code that it may run.

The controller 400 may be connected to the scanning assembly 100, the contouring assembly 200 and the sterilization assembly 300 via wireless and/or wired connections, and may thereby control the operations and functionalities of each assembly 100, 200, 300. For example, the controller 400 may communicate with the assemblies 100, 200, 300 using Bluetooth, Wi-Fi, RF, microwave, telephony, mobile communication protocols or any other types of wireless technologies. The controller 400 may also use LAN, WAN or other types of physical communication connections and/or networks to communicate with the assemblies 100, 200, 300. The controller 400 may also control the operations and functionalities of other assemblies and/or systems as necessary.

The assemblies 100, 200, 300 may also include internal processors and/or controllers, and may thereby perform some or all of their functionalities and operations without the intervention of the controller 400 as necessary. The assemblies 100, 200, 300 may also communicate with each other as necessary using the same or different communication protocols as those described above.

Figure 4A:
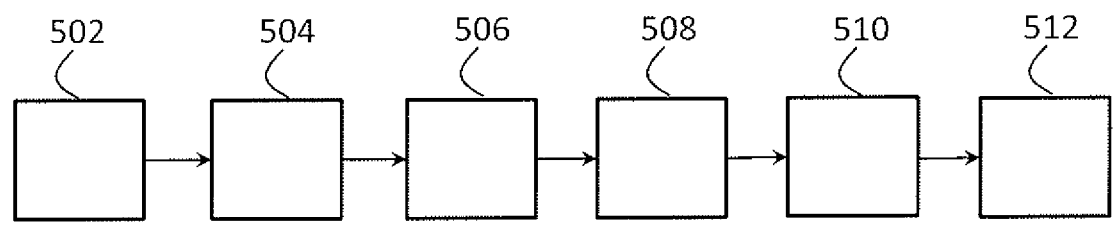

In general, as shown in FIG. 4A, the system 10 may perform the following functionalities:

1. At 502, determine the required curvature(s) in three dimensions of each spinal rod 12 with respect to each corresponding set of implanted pedicle screws 14 and the patient's spine 18;
2. At 504, analyze the three dimensional data to ensure accuracy, quality, viability and other criteria;
3. At 506, interact with the user (e.g., the surgeon) to review, edit and potentially optimize the models of the curvatures and forms of the spinal rods 12;
4. At 508, prepare each spinal rod 12 based on the optimized models;
5. At 510, sterilize each prepared spinal rod 12 (if necessary); and
6. At 512, provide the completed surgical implant to the surgeon for implantation into the patient's body.

Note that the functionalities described above are meant for demonstration and that the system 10 may include all, some, and/or additional functionalities compared to those described. It is also understood that the functionalities listed above may be performed in any order, and that any individual step, or any combinations of any steps, may be performed in different sequences and as many times as required.

Figure 4B:
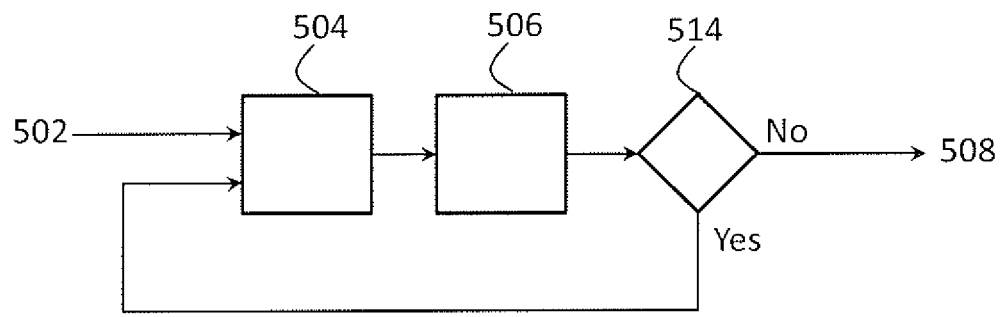

For example, as shown in FIG. 4B, the functionalities and/or steps shown at 504 and 506 may be performed iteratively until an adequate and/or optimal model for the spinal rod 12 may be achieved. For instance, the system 10 at step 514 may make a determination of whether or not the model of the spinal rod 12 was edited by the surgeon in step 506 to a degree that may require the edited model to be re-analyzed.

If the surgeon did in fact edit the model of the spinal rod 12, and the determination is therefore YES at 514, the model may be re-analyzed. If it is determined in step 514 that the model of the spinal rod 12 was not edited in step 506, or at least not edited to a degree that may not warrant re-analyses, then the answer may be NO and the model may be used to create the primary spinal rod 12.

This iterative process may be repeated as many times as desired and/or necessary. Other steps and other functionalities, individually or in combination, of the system 10 may also be taken and/or performed in any sequence as necessary during any iterative process of any other steps.

As mentioned above, prior to the placement of the spinal rod 12, the pedicle screws 14 may first be implanted into the patient's vertebral bodies 24 (as shown in FIGS. 1 and 2). As known in the art, it may be paramount for the pedicle screws 14 to be precisely placed in order to avoid cortical perforations, neurological damage and other health risks for the patient. Accordingly, it may be beneficial to utilize a surgical instrument alignment system as described in U.S. provisional patent application No. 62/763,564: filed on Jun. 6, 2018, and U.S. application Ser. No. 16/140,487, entitled Instrument Alignment Feedback System and Method, the entire contents of which are incorporated herein for any purposes.

The functionalities and steps taken at 502 of FIG. 4A will now be described in further detail with relation to FIG. 5.

Figure 6A:
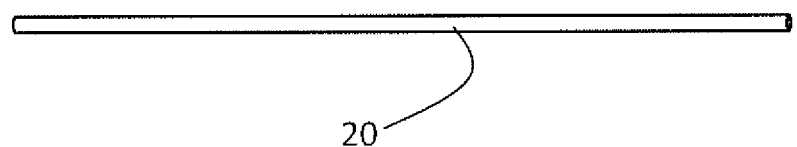
FIG. 6A shows aspects of a surrogate spinal rod according to exemplary embodiments hereof.

In addition, as shown in FIG. 6A, the system 10 may also utilize a malleable surrogate rod 20 (also referred to as a template rod 20). In general, the surrogate rod 20 may be used to determine the required curvature of the final spinal rod 12.

Figure 5:
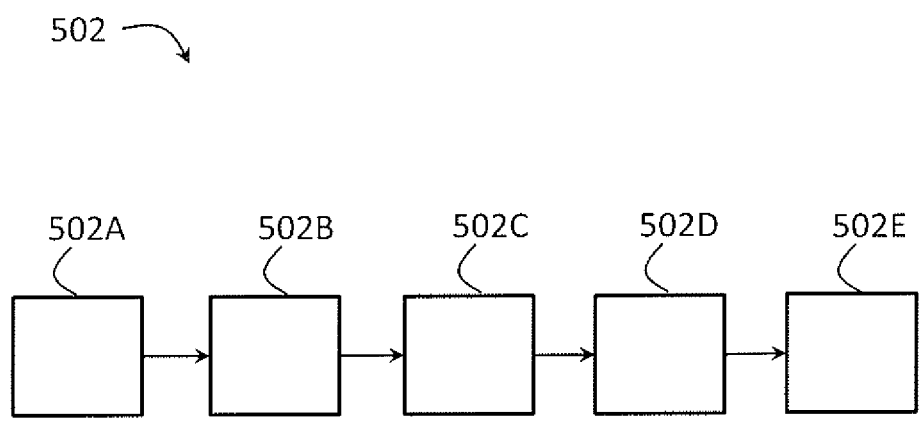
Figure 6B:
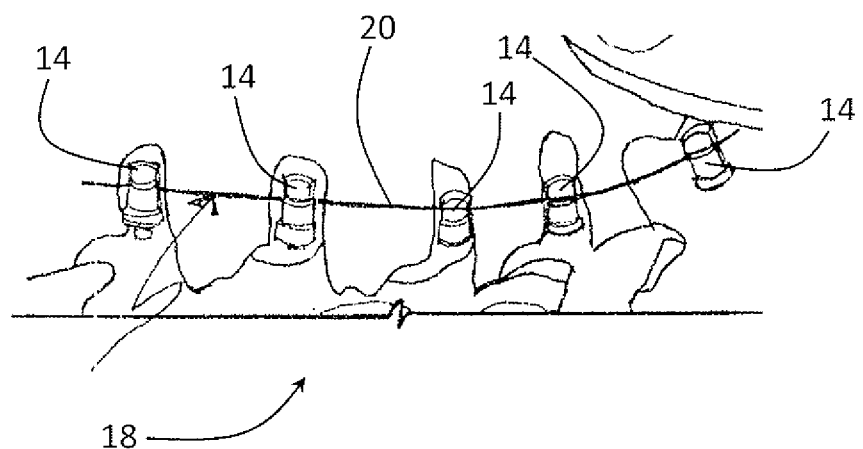
FIG. 6B shows aspects of a surrogate spinal rod attached to pedicle screws according to exemplary embodiments hereof.
Figure 7:
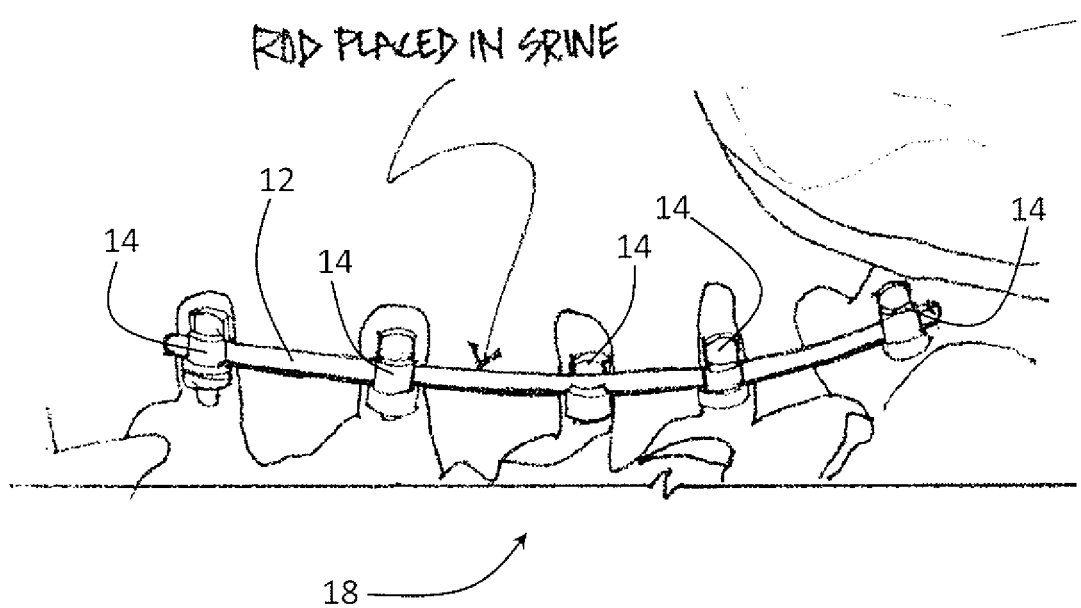
FIG. 7 shows aspects of a spinal rod attached to pedicle screws according to exemplary embodiments hereof.

In step 502A of FIG. 5, with the pedicle screws 14 implanted and in-place within the vertebral bodies 16 of the patient's spine 18, the surrogate rod 20 (sterilized) may be temporarily placed between the screws 14 as shown in FIG. 6B. Because the screws 14 may not be positioned in a linear or otherwise perfectly straight line, the surrogate rod 20 may be manipulated (e.g., contoured, bent, or otherwise formed) in step 502B so that it may fit onto and be properly aligned between the heads of the screws 14. It may be preferable that the surrogate rod 20 be made of a malleable material so that its contour may be formed by hand (e.g., with one's fingers or by using a hand tool such as plyers), but stiff enough that it may hold its form once contoured. For example, the surrogate rod 20 may include a silicon rod with a shape memory core manufactured by Gauthier Biomedical. Other surrogate rods 20 comprising other materials and/or manufactured by other manufacturers may also be used.

Once the surrogate rod 20 has been inserted onto the pedicle screws 14 and properly contoured to fit between them, the surrogate rod 20 may be removed in step 502C and the primary spinal rod 12 may be prepared using the surrogate rod 20 as a template.

In one exemplary embodiment hereof, in step 502D, the contoured surrogate rod 20 may be scanned in three dimensions by the scanner assembly 100 to obtain a three-dimensional (3D) representation (e.g., a CAD file) of the rod 20.

The 3D representation (also referred to as a 3D model) may then be used to form the primary rod 12.

The scanner assembly 100 may include a 3D scanner 102 or other type of imaging device. The scanner 102 may be a tabletop scanner 102, a handheld scanner 102 and/or any other type of 3D scanner 102. If the scanner 102 may be a tabletop scanner, it may include a turntable onto which the surrogate rod 20 may be placed for scanning. The scanner 102 may also include a jig or other type of support structure that may hold the surrogate rod 20 secure during the scanning process.

The scanner 102 may preferably be a non-contact active scanner 102, but may also be a contact scanner 102 and/or a passive scanner 102. The scanner 102 may utilize any technology as required to image the surrogate spinal rod 20, such as but not limited to, time of flight, triangulation, conoscopic holography, and other types of technologies. It may also be preferable that the scanner be properly calibrated.

The scanner 102 may be sterilized and positioned within the sterile field of the surgical procedure, or may not be sterilized and positioned outside the field. Sterilization of the scanner 102 may not be required since once the surrogate spinal rod 20 may be scanned, the scanned information may be transmitted to the controller 400 and the surrogate rod 20 may not return to the sterile field.

The scanning process may involve collecting information regarding the surfaces of the surrogate rod(s) 20. This dataset may be referred to as a point cloud and may include a large number of data points, with each data point corresponding to a physical point on the rod 20. For most applications, multiple scans from different perspectives may be required to obtain information regarding each surface of the rod 20 in three dimensions. The scans may then be brought into a common reference system (a process typically referred to as registration or alignment) and then merged to create a complete 3D model.

It may be preferable that the scanning process result in a large number of data points such that the precision of the resulting 3D model may be high. For example, thousands, tens of thousands, hundreds of thousands and even millions of data points may be taken by the scanning assembly 100. The resulting precision of the 3D model of the surrogate rod 20 may preferably be 100 microns (0.1 mm) or less, but other levels of precision may also be adequate.

Using the point cloud obtained by the scanner 102, a 3D model of the surrogate rod 20 may be computed in step 502E by the scanning assembly 100, by the controller 400, by another system or controller, or by any combination thereof. The model may preferably include a CAD file (e.g., a STEP file, a STP file, a STL file, an IGES file, and other types of files), but other types of files may also be utilized. For the purposes of this specification, the resulting 3D model of the surrogate 20 may be referred to as the rod model 22.

Once the rod model 22 has been formed, the controller 400 may analyze the model 22 in order to ensure accuracy, quality, viability and other criteria (step 504 of FIG. 4A).

In one example, the controller 400 may compare the rod model 22 with imaging data of the patient's spine obtained prior. For example, prior to the surgical procedure, the patient's spine may be stabilized and imaged using a fluoroscopic imaging system or other type of system. A sequence of images may be taken and used to construct a one, two and/or three dimensional model(s) of the patient's spine 18. For the purposes of this specification, this spinal model will be referred to as the pre-surgical spinal model 24.

The pre-surgical spinal model 24 may then be used to model, calculate or otherwise determine the desired position, alignment and trajectory of each pedicle screw and each corresponding spinal rod that may be required during the spinal surgery. It is understood that this data may be theoretically based on the pre-surgical spinal model 24. This information may include, but is not be limited to, the entry point, angular orientation, and trajectory of each pedicle screw, the location, orientation and/or position of each associated spinal rod(s), as well as other information and/or any combinations of information thereof. For the purposes of this specification, the modeled spinal rod information will be referred to as the pre-surgical rod model 26.

The controller 400 may then compare the rod model 22 with the pre-surgical rod model 26 (preferably in three dimensions) to ensure that both models 22, 26 generally follow the same or similar path. If the rod model 22 deviates from the pre-surgical rod model 26 by an amount greater than a predefined threshold, the controller 400 may notify the user of the deviation. The user may then analyze the data to determine if the deviation is due to a problem with the rod model 22, or if the deviation is due to a change that may have occurred with the patient's spine 18.

For instance, if the patient's spine 18 may have changed position from the time of the pre-surgical imaging to the time of the surgery, this may account for the deviation between the pre-surgical rod model 26 and the rod model 22. In addition, the pedicle screws 14 that may be implanted into the patient's spine 18 during the surgery may not match (in position, alignment and trajectory) the theoretical pedicle screw positioning used to calculate the pre-surgical spinal rod model 26. In this case, the rod model 22 may correctly deviate from the pre-surgical rod model 26 due to the fact that the actual implanted pedicle screws 14 may be in slightly different positions and orientations than those modeled, and may therefore require the rod model 22 to follow a different path between them.

In another example, the controller 400 may compare the rod model 22 to the pre-surgical spinal model 24 to ensure that the rod model 22 properly follows the desired contour in relation to the spinal model 24. This may be preferable if the spinal rod 12 may be used to correct the alignment of the patient's spine 18. Deviations between the rod model 22 and the pre-surgical spinal model 24 may then be provided (e.g., displayed) to be analyzed by the surgeon.

The controller 400 may also perform mechanical analyses such as load bearing, stress and failure analyses on the spinal rod model 22 and the surgically implanted pedicle screws 14 separately and in combination. After the pedicle screws 14 may be implanted, images may be taken of the screws 14 within the patient's spine 18, and converted into one, two and/or three-dimensional model(s) of the spine/screw combinations. The controller 400 may then digitally combine the rod model(s) 22 with the spine/screw model(s) to create complete model(s) of the spine 18, the implanted pedicle screws 14 and the rod models 22 in combination. These models may represent the potential outcome of the surgical procedure after the spinal rod 12 may be attached to the implanted pedicle screws 14.

Using these complete models, the controller 400 may perform a number of different tests and analyses. For example, the controller 400 may perform stress and/or failure analyses on the rod model 22 to ensure that its mechanical integrity may not be compromised by the stresses that may be applied to it by the pedicle screws 14 and/or the patient's spine 18.

In addition, by knowing the diameter, length and type of the implanted pedicle screws 14, and the density coefficient of the vertebral body 16, the controller 400 may calculate the pull-out strength of each screw 14 (e.g., the amount of force that may be required to pull the implanted screw 14 out of the bone). The controller 400 may also perform load bearing analyses on the complete models to calculate the forces that may be applied to the pedicle screws 14 by the spinal rods and the spine of the patient. The controller 400 may then compare these forces to the calculated pull-out strength of the screws 14 to ensure that the forces applied to the screws 14 may not be great enough to pull the screws 14 out of the patient's spine 18.

The controller may also perform stress analyses on the model of the patient's spine using the complete models. That is, the controller may calculate or otherwise predict the different forces that may be applied to the spine 18 when the spinal rod 12 may be connected to the implanted pedicle screws 14 in their current arrangements. In this way, the system 10 may ensure that the implants, including the pedicle screws 14 and the spinal rods 12, may not cause undesirable stress and/or strain to the patient's spine after the procedure has been completed.

It is understood by a person of ordinary skill in the art, upon reading this specification, that the tests and analyses performed by the controller 400 as described above are meant for demonstration, and that the controller 400 may perform any types of tests and/or analyses that may be beneficial to the surgical procedure being performed and/or the surgical implant being used. It is also understood that the scope of the system 10 is not limited in any way by the types of tests and/or analyses that the controller 400 may perform.

In step 506 of FIG. 5, the controller 400 may display the results of the various analyses in easy to understand data charts, comparison charts, data overlays, figures and other types of data presentation techniques. In this way, the user may easily review the data results to determine any potential problems with the spinal rod model(s) 22, the positions, alignment and trajectories of the implanted pedicle screw(s) 14, the patient's spine 18, and/or any combination thereof. The controller 400 may include software wizards or other types of interactive tools that may guide the user through the review of each analysis that the controller 400 may perform.

The controller 400 may also provide software wizards or other types of interactive tools that may allow the user to edit the rod model(s) 22 as he/she may deem necessary based on the results of the analyses. For example, the controller 400 may provide tools to view and edit the CAD file of the rod model 22 in real time to adjust its curvature, shape and form.

If the rod model 22 has been modified, the controller 400 may recognize the modification and may advise the surgeon of the potential need to re-analyze the newly modified rod model 22 (in addition to the pedicle screws model, the spinal model, and/or any combination thereof) to ensure that the modified models may all pass the various criteria as described above. The system 10 may require the re-analyses outright, or may allow the surgeon to decide at his/her discretion whether or not the edits performed to the rod model 22 may warrant the re-analyses by the controller 400. This is shown in step 514 of FIG. 4B.

Note that the controller 400 and/or the surgeon may also determine, based on the results of the various analyses or otherwise, that a problem with the rod model 22 may possibly be due to a mistake made in step 502A and/or 502B during the placement and contouring of the surrogate rod 20 within the implanted pedicle screws 14. In this case, the system 10 may advise the surgeon that a second surrogate rod 20' may be used to confirm the initial rod model 22.

Accordingly, the process may return to step 502A with a second surrogate rod 20' that may be placed and contoured within the implanted pedicle screws 14. The second surrogate rod 20' may then be removed in step 502C and scanned in step 502D. A new 3D rod model 22' may be constructed in step 502E.

The controller 400 may then compare the original rod model 22 with the second rod model 22' (preferably in three dimensions). If the rod models 22, 22' overlay within a predetermined threshold, it may be deemed that the rod models 22, 22' are accurate, and the models 22, 22' may be verified. However, if the models 22, 22' deviate from one another by more than a predetermined threshold, it may be deemed that there exists a problem with either the first rod model 22 and/or the second rod model 22', and the process may be repeated until correlation between at least two successive rod models 22 is achieved.

Once the rod model 22 has been optimized and verified, the rod model 22 may be passed to the contouring assembly 200 and be used as a template to create the primary spinal rod 12 (step 508). The model 22 may be passed to the contouring assembly 200 using wireless communication protocols such as Bluetooth, Wi-Fi, RF, microwave, telephony, mobile communication protocols or any other types of wireless technologies. The rod model 12 may also be passed to the contouring assembly 200 using LAN, WAN or other types of physical communication connections and/or networks. However, it may be preferable that wireless communications be used in order to ensure a sterile environment, especially if the scanning assembly 100 may be positioned outside the sterile field of the surgical procedure.

In one exemplary embodiment hereof, the contouring assembly 200 may include a wire and/or rod bending machine 202 (preferably automatic) that may receive the rod model 22 (e.g., the CAD file from the controller 400) and construct a physical spinal rod 12 based on the model 22.

The rod bending machine 202 may preferably be a computer numerical control (CNC) machine with high precision, but other types of rod bending machines 202 may also be used.

It may be preferable that the machine 202 be sterilized and/or located within the sterile field of the surgical procedure. In this way, the rod bending machine 202 may contour a sterile spinal rod 12 and the rod 12 may remain sterile as it is passed from the machine 202 to the surgeon to be surgically placed within the patient.

The spinal rod 12 may be a rod 12 that may be approved for use with the implanted pedicle screws 14 by the US Food and Drug Administration (FDA). It may be preferable that the spinal rod 12 (prior to being contoured) be sterilized and located within the sterile field of the surgery. The sterile spinal rod 12 may then be placed into the sterile rod bending machine 202 to be contoured.

The rod bending machine 202 may preferably have the capability to bend rods of at least the diameter of the spinal rods 12. It may also be preferable that the rod bending machine 202 be capable of bending rods made of the materials used to make the spinal rods 12. For example, it may be preferable that the machine 202 be capable of bending stainless steel, pure titanium, and/or titanium alloy rods 12 of the desired stiffness and diameter.

It may be preferable that the rod bending machine 202 be capable of bending the spinal rod 12 within the precision and accuracy required by the surgical procedure. For example, it may be preferable that the rod bending machine 202 have a bend accuracy of +/−0.5° and a feed accuracy of +/−0.004 inches (0.1 mm). However, machines 202 with other bending accuracies may also be used.

It may also be preferable that the rod bending machine 202 operate quickly such that the spinal rods 12, once inserted into the machine 202, may be produced in a matter of seconds or minutes.

It may also be preferable that the rod bending machine 202 be modular, compact and relatively small in size. In this way, the machine 202 may not take up a significant amount of space and may fit within the sterile field. However, rod bending machines 202 of any size may be used.

In one exemplary implementation, the rod bending machine may be manufactured by D.I. Wire (Pensa Labs), model D.I. Wire Pro or D.I. Wire Plus. However, other rod bending machines 202 may also be used.

If the rod bending machine 202 may not be located within the sterile field of the surgical procedure, or if the rod bending machine 202 may not be adequately sterile, the contoured spinal rod 12 produced by the rod bending machine 202 may be sterilized by the sterilization assembly 300.

The sterilization assembly 300 may include any type of sterilization machine 302 that may provide sterilization of the surgical rod 12 to the standards as required by the surgical procedure. For example, the sterilization machine 302 may include, but is not limited to, a medical washer, an autoclave machine, or any other type of sterilization machine 302 or any combination thereof.

Once the spinal rod 12 has been properly contoured by the contouring assembly 200, and sterilized (if necessary) by the sterilization assembly 300, the sterilized and contoured spinal rod 12 may be passed to the surgeon and attached to the implanted pedicle screws 14 within the patient's spine 18.

Benefits of the System

The benefits of the system 10 are multifold and include, without limitation:

First, the system 10 produces precisely contoured spinal rods 12 using an automatic rod bending machine 202, with the contours based directly on the actual positions of the implanted pedicle screws 14 and the intraoperative positioning of the patient's spine 18. This is accomplished through the contouring and scanning of the surrogate rod 20. As such, the rod model 22 takes into account the exact position, alignment and trajectory of the pedicle screws 14 as they exist within the patient's spine 18, not as they were modeled prior to surgery. Accordingly, the high precision of the rod bending machine 202 is transferred to the resulting spinal rods 12 by the use of the highly accurate intraoperative rod model 22.

This is in sharp contrast with other automatic rod bending systems that may contour the spinal rod 12 based on pre-surgical imaging of the patient's spine 18 and theoretical models of the corresponding pedicle screws 14.

Second, having a highly accurate intraoperative rod model 22, the system 10 is able to perform complex mechanical analyses on the model 22 individually, and in combination with the intraoperative images of the pedicle screws 14 and/or of the spine 18. For example, the system 10 may perform load bearing, stress, failure and pull-out analyses on the elements (screws 14, spine 18 and rods 20). The analyses may be extremely accurate due to the fact that they are based on real time data of each element as they exist during the surgical procedure. This accuracy may be directly proportional to the success of the surgical procedures and to the overall health of the patients.

This differs sharply from other systems that may perform mechanical analyses on the elements based on pre-surgical imaging and theoretical models of the element positions, thus producing less accurate results.

Third, having a highly accurate intraoperative rod model 22, the system may compare the rod model 22 to a pre-surgical rod model that may be obtained based on pre-surgical imaging. This may inform the surgeon of changes that may have taken place with the patient's spine between the time of the pre-surgical imaging and the surgical procedure. This comparison may also be used as an additional verification check to ensure that the rod model 22 is accurate. Other systems operating without this data cannot make this comparison and/or verification.

Fourth, by using highly precise and fast scanners 102 and rod bending machines 202 to scan and contour the spinal rod 12, the spinal rod 12 may be contoured very rapidly (in seconds or minutes). This may lessen the amount of time required for the surgery, and thus, the amount of time that the patient may be required to be under anesthesia. As is known in the art, reducing the amount of time for the surgical procedure may reduce the risk to the patient. Also, with the high cost of operating rooms, this may also reduce the overall cost of the surgical procedures.

Fifth, if the patient may exhibit symptoms of neurological problems (e.g., pain, numbness, limited movement, paralysis, etc.) after the surgical process has been completed, new imaging may be taken of the patient's spine 18 in combination with the implanted pedicle screws 14 and spinal rods 12. The new images may then be compared to the models used during the surgical process (as described above) to determine if a change may have occurred with any of the elements (e.g., the patient's spine 18, the implanted pedicle screws 14, the implanted spinal rods 12, etc.) from the time of the surgical procedure to the time that the symptoms may arise. If the intraoperative models correlate to the post-surgical models, it may be deemed that the elements may not have changed and that the cause of the symptoms may be found elsewhere. However, if the models do not correlate, it may be deemed that a change may have occurred with one or more of the elements and revision of the elements may be necessary.

It is understood by a person of ordinary skill in the art, upon reading this specification, that the use of the controller 400 to perform the various analyses intraoperatively makes it possible for the analyses to be performed. Performing the analyses using other techniques (e.g., manually) would be extremely time consuming and could not be performed intraoperatively within the time constraints of the surgical procedure (e.g., within the maximum amount of time that the patient may be under anesthesia without significant health risks). In this way, the use of the controller improves the process by which the surgical implants may be analyzed, verified and ultimately contoured. The improvements include speed, accuracy and precision, all of which are paramount for a successful surgical outcome.

Those of ordinary skill in the art will appreciate and understand, upon reading this description, that embodiments hereof may provide different and/or other advantages, and that not all embodiments or implementations need have all advantages.

Computing

The functionalities, applications, services, mechanisms, operations, and acts shown and described above are implemented, at least in part, by software running on one or more computers (e.g., the controller 400).

Programs that implement such methods (as well as other types of data) may be stored and transmitted using a variety of media (e.g., computer readable media) in a number of manners. Hard-wired circuitry or custom hardware may be used in place of, or in combination with, some or all of the software instructions that can implement the processes of various embodiments. Thus, various combinations of hardware and software may be used instead of software only.

One of ordinary skill in the art will readily appreciate and understand, upon reading this description, that the various processes described herein may be implemented by, e.g., appropriately programmed computers, special purpose computers and computing devices. One or more such computers or computing devices may be referred to as a computer system.

Figure 8:
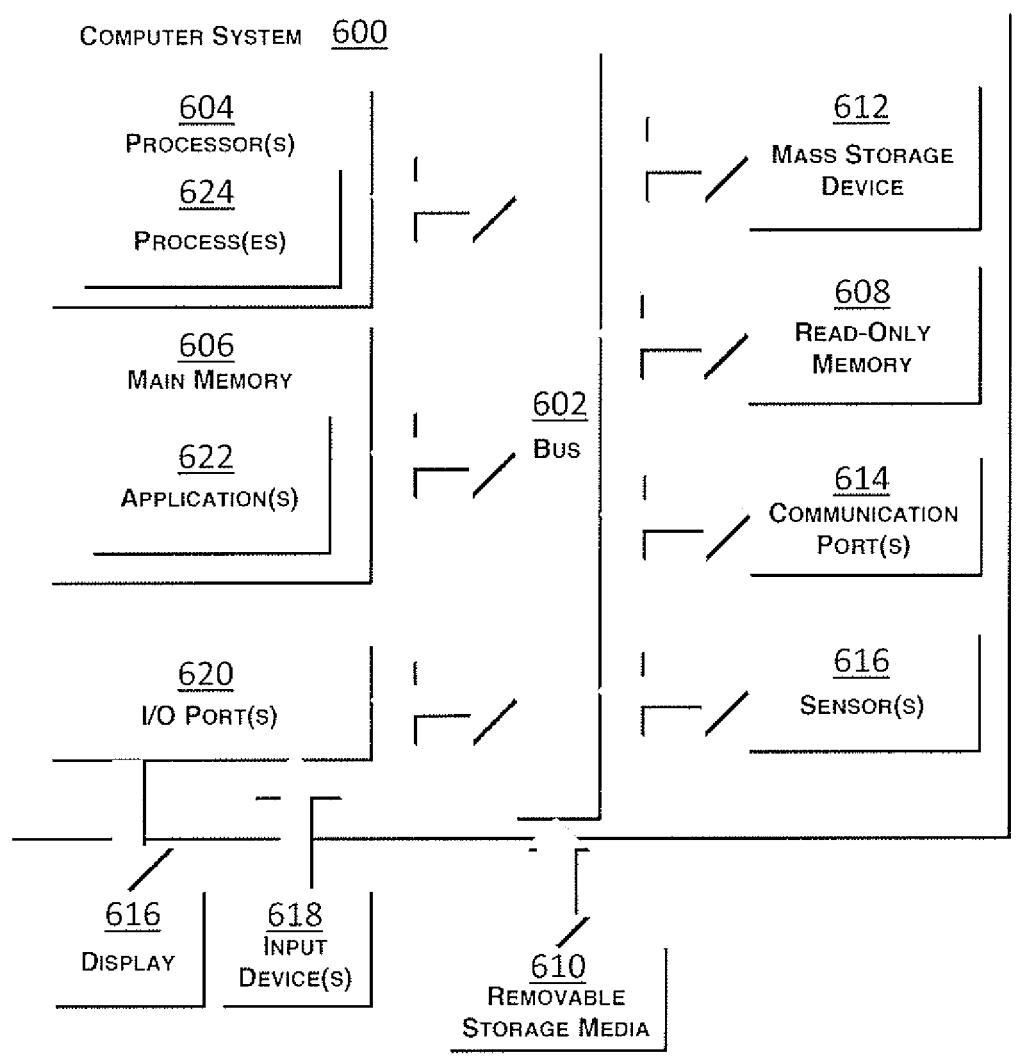
FIG. 8 shows aspects of a computing system according to exemplary embodiments hereof.

FIG. 8 is a schematic diagram of a computer system 600 upon which embodiments of the present disclosure may be implemented and carried out.

According to the present example, the computer system 600 includes a bus 602 (i.e., interconnect), one or more processors 604, a main memory 606, read-only memory 608, removable storage media 610, mass storage 612, and one or more communications ports 614. Communication port(s) 614 may be connected to one or more networks (not shown) by way of which the computer system 600 may receive and/or transmit data.

As used herein, a "processor" means one or more microprocessors, central processing units (CPUs), computing devices, microcontrollers, digital signal processors, or like devices or any combination thereof, regardless of their architecture. An apparatus that performs a process can include, e.g., a processor and those devices such as input devices and output devices that are appropriate to perform the process.

Processor(s) 604 can be any known processor, such as, but not limited to, an Intel® Itanium® or Itanium 2® processor(s), AMD® Opteron® or Athlon MP® processor(s), or Motorola® lines of processors, and the like. Communications port(s) 614 can be any of an Ethernet port, a Gigabit port using copper or fiber, or a USB port, and the like. Communications port(s) 614 may be chosen depending on a network such as a Local Area Network (LAN), a Wide Area Network (WAN), or any network to which the computer system 600 connects. The computer system 600 may be in communication with peripheral devices (e.g., display screen 616, input device(s) 618) via Input/Output (I/O) port 620.

Main memory 606 can be Random Access Memory (RAM), or any other dynamic storage device(s) commonly known in the art. Read-only memory (ROM) 608 can be any static storage device(s) such as Programmable Read-Only Memory (PROM) chips for storing static information such as instructions for processor(s) 604. Mass storage 612 can be used to store information and instructions. For example, hard disk drives, an optical disc, an array of disks such as Redundant Array of Independent Disks (RAID), or any other mass storage devices may be used.

Bus 602 communicatively couples processor(s) 604 with the other memory, storage and communications blocks. Bus 602 can be a PCI/PCI-X, SCSI, a Universal Serial Bus (USB) based system bus (or other) depending on the storage devices used, and the like. Removable storage media 610 can be any kind of external storage, including hard-drives, floppy drives, USB drives, Compact Disc-Read Only Memory (CD-ROM), Compact Disc-Re-Writable (CD-RW), Digital Versatile Disk-Read Only Memory (DVD-ROM), etc.

Embodiments herein may be provided as one or more computer program products, which may include a machine-readable medium having stored thereon instructions, which may be used to program a computer (or other electronic devices) to perform a process. As used herein, the term "machine-readable medium" refers to any medium, a plurality of the same, or a combination of different media, which participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory, which typically constitutes the main memory of the computer. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications.

The machine-readable medium may include, but is not limited to, floppy diskettes, optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols; and/or (iv) encrypted in any of a variety of ways well known in the art.

A computer-readable medium can store (in any appropriate format) those program elements which are appropriate to perform the methods.

As shown, main memory 606 is encoded with application(s) 622 that support(s) the functionality as discussed herein (the application(s) 622 may be an application(s) that provides some or all of the functionality of the services/mechanisms described herein. Application(s) 622 (and/or other resources as described herein) can be embodied as software code such as data and/or logic instructions (e.g., code stored in the memory or on another computer readable medium such as a disk) that supports processing functionality according to different embodiments described herein.

During operation of one embodiment, processor(s) 604 accesses main memory 606 via the use of bus 602 in order to launch, run, execute, interpret or otherwise perform the logic instructions of the application(s) 622. Execution of application(s) 622 produces processing functionality of the service related to the application(s). In other words, the process(es) 624 represent one or more portions of the application(s) 622 performing within or upon the processor(s) 604 in the computer system 600.

It should be noted that, in addition to the process(es) 624 that carries (carry) out operations as discussed herein, other embodiments herein include the application 622 itself (i.e., the un-executed or non-performing logic instructions and/or data). The application 622 may be stored on a computer readable medium (e.g., a repository) such as a disk or in an optical medium. According to other embodiments, the application 622 can also be stored in a memory type system such as in firmware, read only memory (ROM), or, as in this example, as executable code within the main memory 606 (e.g., within Random Access Memory or RAM). For example, application(s) 622 may also be stored in removable storage media 610, read-only memory 608, and/or mass storage device 612.

Those of ordinary skill in the art will understand that the computer system 600 can include other processes and/or software and hardware components, such as an operating system that controls allocation and use of hardware resources.

As discussed herein, embodiments of the present invention include various steps or operations. A variety of these steps may be performed by hardware components or may be embodied in machine-executable instructions, which may be used to cause a general-purpose or special-purpose processor programmed with the instructions to perform the operations. Alternatively, the steps may be performed by a combination of hardware, software, and/or firmware. The term "module" refers to a self-contained functional component, which can include hardware, software, firmware or any combination thereof.

One of ordinary skill in the art will readily appreciate and understand, upon reading this description, that embodiments of an apparatus may include a computer/computing device operable to perform some (but not necessarily all) of the described process.

Embodiments of a computer-readable medium storing a program or data structure include a computer-readable medium storing a program that, when executed, can cause a processor to perform some (but not necessarily all) of the described process.

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

It should be appreciated that the words "first," "second," and so on, in the description and claims, are used to distinguish or identify, and not to show a serial or numerical limitation. Similarly, letter labels (e.g., "(A)", "(B)", "(C)", and so on, or "(a)", "(b)", and so on) and/or numbers (e.g., "(i)", "(ii)", and so on) are used to assist in readability and to help distinguish and/or identify, and are not intended to be otherwise limiting or to impose or imply any serial or numerical limitations or orderings. Similarly, words such as "particular," "specific," "certain," and "given," in the description and claims, if used, are to distinguish or identify, and are not intended to be otherwise limiting.

As used herein, including in the claims, the terms "multiple" and "plurality" mean "two or more," and include the case of "two." Thus, e.g., the phrase "multiple ABCs," means "two or more ABCs," and includes "two ABCs." Similarly, e.g., the phrase "multiple PQRs," means "two or more PQRs," and includes "two PQRs."

The present invention also covers the exact terms, features, values and ranges, etc. in case these terms, features, values and ranges etc. are used in conjunction with terms such as about, around, generally, substantially, essentially, at least etc. (i.e., "about 3" or "approximately 3" shall also cover exactly 3 or "substantially constant" shall also cover exactly constant).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components unless specifically so stated.

It will be appreciated that variations to the embodiments of the invention can be made while still falling within the scope of the invention. Alternative features serving the same, equivalent or similar purpose can replace features disclosed in the specification, unless stated otherwise. Thus, unless stated otherwise, each feature disclosed represents one example of a generic series of equivalent or similar features.

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

Use of exemplary language, such as "for instance", "such as", "for example" ("e.g.,") and the like, is merely intended to better illustrate the invention and does not indicate a limitation on the scope of the invention unless specifically so claimed.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

What is claimed is:

1. A system for intraoperatively contouring a spinal rod for placement onto the spine of a patient, comprising:
   a first contoured surrogate spinal rod,
   a second contoured surrogate spinal rod,
   a scanning assembly configured to scan the first contoured surrogate spinal rod and to output a first model based on the scan, and to scan the second contoured surrogate spinal rod and to output a second model based on the scan;
   a controller configured to receive the first model and to perform at least one analysis on the first model; and
   a contouring assembly configured to receive the first model from the controller and to contour the spinal rod based on the first model,
   wherein the contour of the first and the second contoured surrogate spinal rod is based at least in part on the intraoperative position of one or more pedicle screws implanted into the patient's spine,
   wherein the controller creates the second model based at least in part on the first model, the intraoperative position of the one or more pedicle screws and the position of the patient's spine; and
   wherein the controller is configured to compare the first and second model to determine whether they deviate from each other by more than a predetermined threshold.

2. The system of claim 1 wherein the controller is configured to provide feedback relating to the results of the at least one analysis.

3. The system of claim 1 wherein the at least one analysis is based at least in part on the intraoperative position of the one or more pedicle screws and the position of the patient's spine.

4. The system of claim 3 wherein the at least one analysis is chosen from the group consisting of: load bearing analysis, stress analysis and failure analysis.

5. The system of claim 1 wherein the controller performs at least one analysis on the second model.

6. The system of claim 5 wherein the at least one analysis is chosen from the group consisting of: load bearing analysis, stress analysis and failure analysis.

7. The system of claim 5 wherein the results of the at least one analysis are compared with the pull-out strength of the one or more pedicle screws.

8. The system of claim 5 wherein the controller is configured to provide feedback relating to the results of the at least one analysis.

9. The system of claim 7 wherein the controller is configured to provide feedback relating to the comparison.

10. The system of claim 1 wherein the scanning assembly is a three dimensional scanner.

11. The system of claim 1 wherein the contouring assembly is a rod bending machine.

12. The system of claim 1 wherein the first model is a three dimensional model of the contoured surrogate spinal rod.

13. A method for intraoperatively contouring a spinal rod using a system comprising:
    a first and second contoured surrogate spinal rod;
    a scanning assembly;
    a controller; and
    a contouring assembly;
    the method comprising:
    (A) using the scanning assembly, scanning the first contoured surrogate spinal rod to create a first model;
    (B) using the controller, performing at least one analysis on the first model created in (A);
    (B)(1) using the controller, creating a second model from the second contoured surrogate spinal rod and also based at least in part on the first model, the intraoperative position of one or more pedicle screws implanted into the patient's spine, and the position of the patient's spine;
    (B) (3) comparing the first and second model to confirm that they do not deviate from each other by more than a predetermined threshold;
    (C) using the controller, providing feedback relating to the results of the at least one analysis performed in (B);
    (D) providing the first model to the contouring assembly; and
    (E) using the contouring assembly, contouring the spinal rod based on the model created in (A).

14. The method of claim 13 wherein the at least one analysis in (B) is chosen from the group consisting of: load bearing analysis, stress analysis and failure analysis.

15. A method for intraoperatively contouring a spinal rod using a system comprising:
    a first and second contoured surrogate spinal rod;
    a scanning assembly;
    a controller; and
    a contouring assembly;
    the method comprising:
    (A) using the scanning assembly, scanning the first contoured surrogate spinal rod to create a first model, and scanning the second contoured surrogate spinal rod to create a second model;
    (B) using the controller, performing at least one analysis on the first model created in (A);
    (B)(2) using the controller, performing at least one analysis on the second model;
    (B) (3) using the controller, comparing the first and second model to confirm that they do not deviate from each other by more than a predetermined threshold;
    (C) using the controller, providing feedback relating to the results of the at least one analysis performed in (B);
    (D) providing the first model to the contouring assembly; and
    (E) using the contouring assembly, contouring the spinal rod based on the first model created in (A).

16. The method of claim 15 wherein the at least one analysis in (B)(2) is chosen from the group consisting of: load bearing analysis, stress analysis and failure analysis.

* * * * *